United States Patent [19]

Edwards

[11] 4,198,526
[45] Apr. 15, 1980

[54] PROCESS FOR THE MANUFACTURE OF P-HYDROXYPHENYL ACETIC ACID

[75] Inventor: Philip N. Edwards, Macclesfield, England

[73] Assignee: Imperial Chemical Industries Limited, London, England

[21] Appl. No.: 908,466

[22] Filed: May 22, 1978

[51] Int. Cl.$^2$ ............................................. C07C 65/02
[52] U.S. Cl. ..................................................... 562/478
[58] Field of Search ......................................... 562/478

[56] References Cited

PUBLICATIONS

March, J. Adv. Org. Chem. p. 402, 2nd Ed. Copyright in 1968.

Primary Examiner—Paul J. Killos
Attorney, Agent, or Firm—Cushman, Darby & Cushman

[57] ABSTRACT

A process for the manufacture of p-hydroxyphenylacetic acid by the reduction of p-hydroxymandelic acid. The product is a useful intermediate for the preparation of the β-adrenergic blocking agent atenolol.

3 Claims, No Drawings

PROCESS FOR THE MANUFACTURE OF P-HYDROXYPHENYL ACETIC ACID

This invention relates to a new reduction process and in particular it relates to a reduction process for the manufacture of p-hydroxyphenylacetic acid which is a valuable chemical intermediate.

According to the invention there is provided a process for the manufacture of p-hydroxyphenylacetic acid which comprises the reduction of p-hydroxymandelic acid.

The reduction may be carried out by catalytic means, for example by means of hydrogen in the presence of a palladium catalyst, or by chemical means, for example by the use of hypophosphorus acid or a salt thereof, or by the use of a chromous salt.

The catalytic hydrogenation may be carried out at a temperature of up to 80° C. and at atmospheric pressure. The reaction is preferably carried out in the presence of a mineral acid, for example hydrochloric acid.

The hydrogenation process is particularly preferably carried out in the presence of chloride ion, which minimises undesirable hydrogenation of the benzene ring. The chloride ion may be provided by hydrochloric acid, or by a metal chloride, for example sodium or potassium chloride, preferably in the presence of a strong acid.

A preferred chemical reduction process may be carried out by means of a chromous salt prepared in situ by the reduction of a chromic salt, for example chromic chloride, with zinc dissolving in an acid, for example using zinc dust in aqueous sulphuric acid.

The p-hydroxymandelic acid used as starting material is a known compound, but it is most conveniently obtained in the form of sodium or potassium p-hydroxymandelate monohydrate as described in co-pending U.S. application Ser. No. 908,465 filed May 22, 1978.

As stated above, p-hydroxyphenylacetic acid is a valuable chemical intermediate, and in particular it is a valuable intermediate for use in the preparation of its amide which in turn is a valuable intermediate for the preparation of the β-adrenergic blocking agent p-(2-hydroxy-3-isopropylaminopropoxy)phenylacetamide (atenolol).

The invention is illustrated but not limited by the following Examples:

EXAMPLE 1

A 5% palladium-on-charcoal catalyst (0.5 g.) is added to a mixture of sodium p-hydroxymandelate monohydrate (4.5 g.), water (25 ml.) and concentrated aqueous hydrochloric acid (6 ml.) and the mixture is stirred magnetically and hydrogenated at a pressure of 1 atmosphere and a temperature of 75° C. using an Englehard Mark II hydrogenation control unit. After 4 hours hydrogen uptake ceases and the hot solution is filtered. The pH of the filtrate is adjusted to 3 and the mixture is concentrated to 10 ml. and then cooled and filtered. The solid product is washed with brine and ice-cold water and then dried. There is thus obtained p-hydroxyphenylacetic acid, m.p. 145°–147° C., in 85% yield.

EXAMPLE 2

A mixture of 65% w/v aqueous chromic chloride solution (16.4 liters) and 78% w/w aqueous sulphuric acid (7.5 liters) is heated to 35° C. and then added very rapidly to a stirred mixture of sodium p-hydroxymandelate monohydrate (16.6 kg.), zinc dust (10.4 kg.), water (28 liters) and paraffin oil (0.35 liters; used to prevent foaming) which is heated to 50° C. The stirred mixture is then heated to 80° C. and further 78% w/w aqueous sulphuric acid (10 liters) is added during 90 minutes. The stirred mixture is heated at 80° C. for a further 75 minutes and is then filtered. The solid residue consists of p-hydroxyphenylacetic acid and is obtained in 97% yield based on the sodium p-hydroxymandelate used.

EXAMPLE 3

A stirred mixture of sodium p-hydroxymandelate monohydrate (21.2 g.), potassium hypophosphite (52 g.), 50% w/v aqueous hypophosphorous acid (2.2. ml.) and water (10 ml.) is heated under reflux for 22 hours (internal temperature 143° C.) and then cooled. The mixture is diluted with water, acidified with hydrochloric acid and extracted with methyl isobutyl ketone. p-Hydroxyphenylacetic acid, which is formed in 67% yield, is isolated from the extract by conventional means.

What I claim is:

1. A process for the manufacture of p-hydroxyphenylacetic acid which comprises reducing p-hydroxymandelic acid by heating the p-hydroxymandelic acid in aqueous acidic solution in the presence of a chromous salt and then recovering the resulting p-hydroxyphenylacetic acid.

2. A process as claimed in claim 1 wherein the chromous salt is prepared in situ by the reduction of a chromic salt with zinc dissolving in an acid.

3. A process as claimed in claim 2 which is carried out by use of chromic chloride and zinc dust dissolving in aqueous sulphuric acid.